United States Patent [19]
Dishler

[11] Patent Number: 5,807,380
[45] Date of Patent: Sep. 15, 1998

[54] OPTICAL GUIDE AND METHOD FOR USE IN CORRECTIVE LASER EYE SURGERY

[76] Inventor: Jon G. Dishler, 6295 S. Macon Way, Englewood, Colo. 80111

[21] Appl. No.: 639,127

[22] Filed: Apr. 26, 1996

[51] Int. Cl.$^6$ .................................................. A61M 35/00
[52] U.S. Cl. .................................... 606/5; 606/4; 606/166
[58] Field of Search .................................... 606/4, 5, 6, 10, 606/11, 12, 166

[56] References Cited

U.S. PATENT DOCUMENTS

| | | | |
|---|---|---|---|
| 4,905,711 | 3/1990 | Bennett et al. | 606/4 X |
| 5,092,863 | 3/1992 | Schanzlin | 606/5 |
| 5,108,412 | 4/1992 | Krumeich et al. | 606/4 X |
| 5,133,708 | 7/1992 | Smith | 606/5 |
| 5,336,215 | 8/1994 | Hsueh et al. | 606/4 |
| 5,356,409 | 10/1994 | Nizzola | 606/5 |
| 5,490,849 | 2/1996 | Smith | 606/5 |
| 5,582,608 | 12/1996 | Brown | 606/4 |
| 5,586,980 | 12/1996 | Kremer et al. | 606/4 |
| 5,616,139 | 4/1997 | Okamoto | 606/4 |

*Primary Examiner*—Robert L. Nasser
*Attorney, Agent, or Firm*—Timothy J. Martin; Michael R. Henson

[57] ABSTRACT

An optical guide dispenses laser light that is incident outside a selected region during laser eye surgery. The guide is formed as a body with a passageway of selected geometrical cross-section that defines a mininmum optical opening. The body has a material which circumferentially surrounds the passageway that is effective to dispense laser light incident thereto such that the energy thereof is dissipated to a level that will not affect eye tissue. A handle may optionally be provided to facilitate manipulation of the body. The passageway is preferably frustoconical. An optical system incorporates the optical guide and includes a mount that is to be placed in contact with the eye. The optical guide is secured to the mount, such as by cooperative rails and protrusions. A method is described to perform laser eye surgery using such optical guide and directing laser light along an optical path parallel to the central axis of the passageway. The laser light beam is then moved to follow a pathway that surrounds a central point. The diameter of the beam may be varied.

22 Claims, 3 Drawing Sheets

OPTICAL GUIDE AND METHOD FOR USE IN CORRECTIVE LASER EYE SURGERY

FIELD OF THE INVENTION

The present invention broadly concerns laser surgery, but is particularly directed to refractive eye surgery for correcting visual acuity by reforming the cornea by way of laser removal of tissue. Specifically, the present invention is directed to an optical guide which controls the geometry over which the laser surgery occurs. The present invention also concerns a method for laser surgery using such an optical guide, especially corrective surgery for hyperopia.

BACKGROUND OF THE INVENTION

The value and need visual acuity cannot be overstated. Historically, human beings have relied on eyesight as perhaps the most significant sensory perception employed in interacting with the environment. Unfortunately many persons, however, experience slight aberrations in the physical structure of the eye which aberrations interfere with the maximum acuity possible. These aberrations primarily manifest in three conditions: (1) myopia; (2) hyperopia; and (3) astigmatism.

Myopia is a condition wherein parallel light rays entering the eye are focused in front of the retina such that nearby objects are seen with greater clarity than distant objects. Myopia can be caused by an elongated eyeball or by a cornea which has too steep of a curvature resulting in greater refraction than desired. On the other hand, hyperopia is a condition wherein parallel light rays focus behind the retina so that distant objects are seen more clearly than nearby objects. Hyperopia results where the eyeball is foreshortened or where the curvature of the cornea is not steep enough for proper focusing of light rays onto the retina. Astigmatism is a defect of the eye whereby rays of light converge unequally in different meridians thus causing uneven focus or multiple images to be perceived. Astigmatism typically results where the cornea is slightly ovoid instead of circular.

Until the middle ages, people were generally confined to the visual acuity provided by their respective eye physiology. However, greater understanding of optics lead to the creation of corrective lenses which, when placed in front of the eye, could compensate for visual defects thereby causing a redirection of light whereby the defective eye would focus light onto the retina. As the understanding of both optics and eye physiology grew, lenses became more and more sophisticated. In the present day, lenses can correct for myopia, hyperopia, astigmatism and other eye conditions. Lenses are sometimes designed to have different focusing properties in different sections, such as bifocals and trifocals, in order to compensate for different visual acuity of an eye at different distances.

While the invention of eyeglasses may well be one of the most significant contributions to the quality of human life, at least for those who have visual defects, eyeglasses have their drawbacks. For example, eyeglasses provide a generally conic field of vision defined by that volume which is the geometric projection of the perimeter of the lens from the focal point thereof; thus, there is no enhancement of peripheral vision. Moreover, many people find the wearing of eyeglasses to be somewhat uncomfortable, especially if they are not fit properly. Discomfort can result from the weight of the lenses as well as the frame holding them or an improper fit of the frame to the differing shapes of the human head. During times of high activity wherein the need for visual acuity is often greatest, eyeglasses can tend to become dislodged resulting in a loss of visual acuity at a time when it is especially desired. Finally, some persons perceive the wearing of glasses to be aesthetically unpleasing. Unfortunately, the wearer of eyeglasses may sometimes be self-conscious or openly subjected to derisive comments from others.

As a result of the disadvantages of eyeglasses, efforts were made to create lenses which would fit directly onto the eye which would allow greater peripheral vision, which would be more secure and which would be less noticeable to others. Such a lens, commonly referred to as a "contact lens", had their first major development circa 1945. At the time of inception, these lenses were large shells which fit over substantially the entire exposed surface of the eyeball. These early lenses caused substantial irritation to the eye and to the surrounding tissues. Accordingly, they could only be worn for a short period of time.

Over the next two decades, the physical size of contact lens decreased, and improvements were made in materials technology so that contact lenses came to be made of plastic and were of reduced thickness and diameter. The diameter of the lens was reduced to approximately 8 to 10 millimeters, corresponding to the necessary corrective dimensions needed for the eye over differing light conditions. While these hard plastic lenses were substantial improvements over the earlier glass lenses, they nevertheless still caused the irritation and sometimes pain the wearer. In part this was due to the irritation of the eye and inner surface of the eye lid but it also was a function of diminished oxygen exchange by the lubricating fluids of the eye which were trapped between the eyeball and the lens.

Accordingly, there have been ongoing improvements into contact lens technology. Among these are the development of semi-soft contact lenses, soft lenses, extended wear lenses and gas permeable lenses.

Another avenue investigated for correcting defects in visual acuity has been through eye surgery. Surgery for correcting certain defects in the eye, such as vision obscuring cataracts, dates back approximately two thousand years wherein a needle was inserted into the eye in a manner to dislodge the occluded lens and push it out of the optical path. It was not until the 1960's, however, that significant developments towards surgical correction of the refractive properties of the eye became developed.

One technique pioneered at this time has come to be known as radial keratotomy which can be used to correct mild levels of myopia. In radial keratotomy, the cornea of the eye is slit along a plurality of lines radiating from the pupil with such cuts being made at constant depths. The result is that the cornea relaxes to reduce the steepness of its curvature thereby resulting in a longer focal length. The overall result is that the focal point of the eye is moved rearwardly onto the retina. Radial keratotomy, however, is not available as a treatment for hyperopia since hyperopia requires the creation of a greater lensing effect. Similar in concept to radial keratotomy is astigmatic keratotomy wherein arcuate slits are selectively cut into the eye at desired radial distances so that the ovoid configuration of the cornea becomes more round.

Somewhat contemporaneously with the development of radial keratotomy was the investigation into a technique that became known as, lamellar refractive surgery. A first developed technique was myopic keratomileusis (MKM). Here, a surgeon would cut a dome-like shell or cap off of the cornea and remove a disk of corneal tissue after which the cap was replaced. The removal of the cornea tissue reduced the steepness of the corneal curvature thereby lessening its lensing effect resulting in correction of a myopic condition. This technique had three main drawbacks. First, proper rotational orientation of the corneal cap on replacement was difficult. Second, even after the repositioning of the corneal cap, it was subject to dislodgement and possible loss during the healing process. Third, and significantly, it was difficult for a surgeon to manually cut a uniform disk out of the cornea. Any anomalies in the thickness of the removed disk created non-uniform correction.

Two major advances helped establish MKM as a viable corrective technique. First, the rotational issue of the corneal cap was resolved by developing a technique wherein the dome-like cap was not cut completely off of the cornea but was rather left attached by a small hinge of tissue along one edge. During surgery, this cap was then pivoted out of the way while the corrective tissue disk was removed from the cornea after which the cap was repositioned. The tissue hinge maintained proper orientation and also helped decrease the likelihood of dislodgement and loss of the corneal cap during the healing process. Second, advances in computer technology and better instrumentation resulted in the development of the automated microkeratome. This device, in essence, is an automated scalpel which could be computer controlled to cut a fairly uniform thickness disk out of the cornea after the corneal cap had been cut and pivoted out of position. This could be accomplished directly on the globe portion of the eye and therefore avoid the necessity of freezing the corneal cap as had been the case with MKM. This operative procedure came to be known as automated lamellar keratoplasty (ALK) and its use became more accepted in the late 1980's. This technique was advantageous for its ability to correct more extreme cases of myopia.

Next in the development of surgical techniques for corrective eye surgery was the laser technique known as the excimer laser technique. In this technique, the surface of the cornea is burnt away in a desired configuration by a light intensity laser beam operating at 193 micron wavelength. The laser beam is controlled in intensity and pattern to etch away surface corneal tissue so as to alter its curvature and thereby its refractive properties in order to correct myopic and astigmatic conditions. The excimer laser is a somewhat painful process, though, since it burns away the epithelia layer which requires one to two weeks to heal. In addition, the excimer laser sometimes causes undesired scaring of the cornea. The excimer laser, however, does show substantial promise for correcting mild to medium myopia and astigmatism.

Recently, however, perhaps the most promising of all surgical techniques has been explored using a combination of automated lamellar keratoplasty and the benefits of excimer-type lasers. This procedure, which is known as laser assisted intrastromal keratomileusis (LASIK) involves the cutting of the dome-like corneal cap utilizing the microkeratome. After cutting the cap, the microkeratome is removed from the support assembly and the cap is pivoted out of position. Laser focusing optics are then brought into position over the exposed, domed surface of the cornea formed by removal of the cap shell. The laser light is then very precisely controlled so that a desired contoured shaping of the exposed surface occurs by varying the tracking, intensity and size of the laser beam. After performing the sculpting of the corneal interior, the cap is repositioned and the cornea reheals with a modified curvature.

LASIK surgery is especially promising in that it provides numerous advantages over previous surgical techniques. On one hand, the use of a laser surgical technique can be very precisely controlled, as is the case with traditional excimer surgery so that the cutting of the proper corrective contour can be very precise. In addition, since the removal of tissue occurs in the inside of the cornea, the epithelial layer and the Bowman's layer are not removed so that very little pain and less damage to the cornea occurs. The ability to control the laser also allows for the simultaneous correction of both the necessary refractive prescription as well as correction of astigmatism. The LASIK technique also has the benefit of being able to correct severe degrees of myopia up to approximately 30 diopters. Finally, unlike many of the other techniques, the LASIK procedure holds great promise for its ability to correct hyperopia as well as myopia. This procedure and its relation to the present invention is described more thoroughly in the description of the detailed embodiment section of this application.

In any event, it can be appreciated that there remains a need for improved techniques for corrective eye surgery. The present invention is directed to such need, and this invention concerns corrective eye surgery techniques employing laser surgery. Thus, while the optical guide according to the present invention may possibly be employed with the excimer surgical technique, the present invention is primarily directed to LASIK surgery, and, even more specifically, to the correction of hyperopia by means of the LASIK procedure.

SUMMARY OF THE INVENTION

It is an object of the present invention to provide a new and useful optical guide which may be used in laser based corrective eye surgery.

Another object of the present invention is to provide apparatus and a method for laser surgery to correct hyperopia.

A further object of the present invention is to provide an optical guide and surgery technique for laser surgery which increases the range of sculpted contours which may be formed in the human cornea as a method of corrective eye surgery.

To accomplish these objects, then, the present invention is directed to an optical guide that is adapted for use in laser surgery of an eye with this optical guide being operative to disburse laser light at a selected energy where the laser light is incident areas outside of a selected operating region. Broadly, the optical guide includes a body that has a passageway therethrough with a sidewall surrounding the passageway. The passageway has a selected geometrical cross-section that defines a minimum optical opening within which the laser surgery is performed. This minimum optical opening has a periphery of a selected configuration through which the laser light may pass, but the body is constructed of a material that is effective in disbursing the laser light which is incident thereto such that the energy of the laser light is dissipated to a level that will not effect eye tissues.

In its more specific form, the body portion of the optical guide is annular in shape with the passageway extending axially therethrough and defined by the sidewall of the body. This passageway is preferably frustoconical in shape so that the sidewall is angularly divergent in a direction from a bottom portion faced adjacent to the eye to a top portion thereof. This angle of divergence is preferably about 30°. The body portion is preferably fabricated of a plastic material, namely polymethyl methacrylate, although other plastic materials may likely be used. Indeed, glass compositions may be employed, as well. Also, a handle member may be secured to the body, with the handle member being operative to facilitate manipulation of the body member.

The present invention is also directed to an optical system for use in corrective eye surgery wherein focusing optics directs a beam of laser light from a laser light source of a selected energy along an optical path that is then sent onto tissues of an eye and wherein a control system is provided to control the size of the beam of laser light and a tracking path for this beam used during surgery. The optical system, then, includes an optical guide of the type described above, with this optical guide being adapted to be secured to a mount that is operative which is placed in contact with the eye over a region targeted for laser surgery. This mount is preferably a suction ring handle that has a pair of parallel rail elements arranged in spaced apart facing relationship to one another. The optical guide then includes an engagement structure sized and configured to engage the rails thereby to assist in securing the optical guide to the mount. This engagement structure preferably includes a foot portion operative to engage one of the rails and a shoulder portion disposed oppositely of the foot portion and operative to engage another of the rails by spanning the same. The mount may then include a retaining element operative to bear against the body portion to attain the foot and the shoulder portion in engagement with the rails. For example, the retaining element may be resiliently biased against the body portion of the optical guide when it is secured to the mount.

Further, the present invention is directed to a method of performing laser eye surgery for correction, specifically, of hyperopia. Broadly, this method comprises a first step of preparing an eye to have an exposed section of corneal tissue. Thereafter, an optical guide is disposed approximately to the exposed section of the corneal tissue with the optical guide including a body portion that has an axial passageway therethrough which permits unobstructed passage of axial laser light to an operative region surrounded by a sidewall of the optical guide with this operative region having a surrounding periphery of selected configuration and a center point such that the axial passageway has a central axis passing through the center point. Next, a beam of laser light is directed along an optical path that is parallel to the central axis so that the laser beam is incident to the exposed section. The beam of laser light is at a selected energy sufficient to remove to corneal tissues cells and has a central area of maximum intensity but which is sized to have a diameter that is greater than a radial dimension of the operative region. The beam of laser light is positioned such that the central area thereof is offset from the center point whereby an active portion of the light that passed through the axial passageway and where an inactive portion of the laser light will be incident to the body portion. The sidewall of the wall optical guide which is disposed proximate to the exposed section of corneal tissue is thus selected of material that is effective in disbursing the energy of the laser light to a level that will not remove corneal tissue cells. Finally, the method includes a step of moving the beam of laser light such that the central area thereof follows a pathway that surrounds the central point so that a recess in the exposed section of corneal tissue is formed by removal of corneal tissue cells.

The step of preparing an eye to have an exposed section of corneal of corneal tissue is accomplished by cutting a shell-like cap off the cornea with this cap being about 150 millimeters in thickness so that the exposed section of corneal tissue is dome shaped. The base of the dome shape of the exposed section is approximately 8 millimeters. The central area of the laser beam is then oriented approximately 2.5 to 3.5 millimeter from the center point. The diameter of the laser beam is varied as the beam is moved along the pathway. For example, the diameter may be expanded. Preferably, the diameter of the beam is varied between 1.0 millimeters and 5.0 millimeters. The pathway is of a selected geometrical shape which may conveniently be a circular pathway or an ovoid pathway.

These and other objects of the present invention will become more readily appreciated and understood from a consideration of the following detailed description of the exemplary embodiment when taken together with the accompanying drawings, in which:

DETAILED DESCRIPTION OF THE EXEMPLARY EMBODIMENT

The present invention is broadly directed to an optical guide that is useful in the corrective surgery of the human eye. This invention is specifically directed to laser surgery of the eye, especially as used to correct hyperopia. Accordingly, in addition to the optical guide described herein, the present invention is also directed to a method of performing corrective laser surgery and, to this end, is directed to a method of performing surgery to correct hyperopia.

In order to gain an understanding of the instruments used and the procedure for performing laser surgery. As noted in the background of the invention, there are two general types of laser surgery, one being the excimer laser technique and the other being the LASIK technique. This invention will be described from the standpoint of the LASIK procedure although it should be appreciated that the device disclosed and claimed herein as well as the operative techniques may have other laser surgery applications including excimer surgery, as well.

According to the prior art, LASIK surgery requires the formation of a shell-like dome or cap that is cut a uniform selected depth into the cornea along a curved surface parallel to the outer surface of the cornea. This cap is transverse to the eye's optical axis and centered thereon. A small piece of connecting tissue is left so as to provide a hinge that allows the cap to be pivoted out of position while remaining attached to the cornea. Typically, the cap is about ten millimeters in diameter and has a thickness of about 150 microns. In order to perform this surgery, a device known as a microkeratome is used to cut the cap with the microkeratome being positioned relative to the eye by a mount of the type shown in FIGS. 1 and 2. This mount is sometimes called a suction ring and handle.

Figures 1, 2:
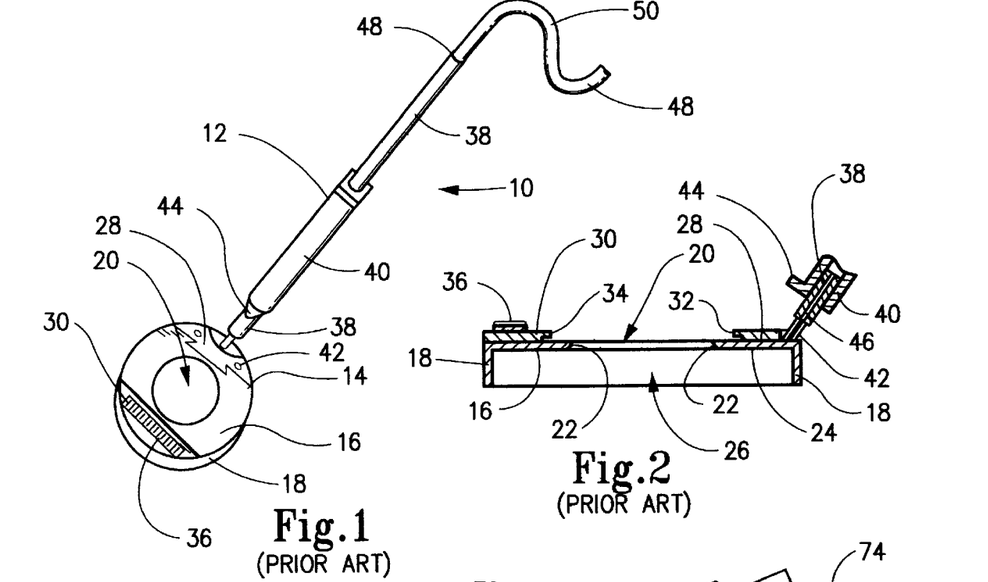
FIG. 1 is a perspective view of a microkeratome interface bracket according to the prior art.
FIG. 2 is a side view in cross-section of the lower portion of the apparatus of FIG. 1 which lower portion contacts the human eye.
Figures 3, 8, 9:
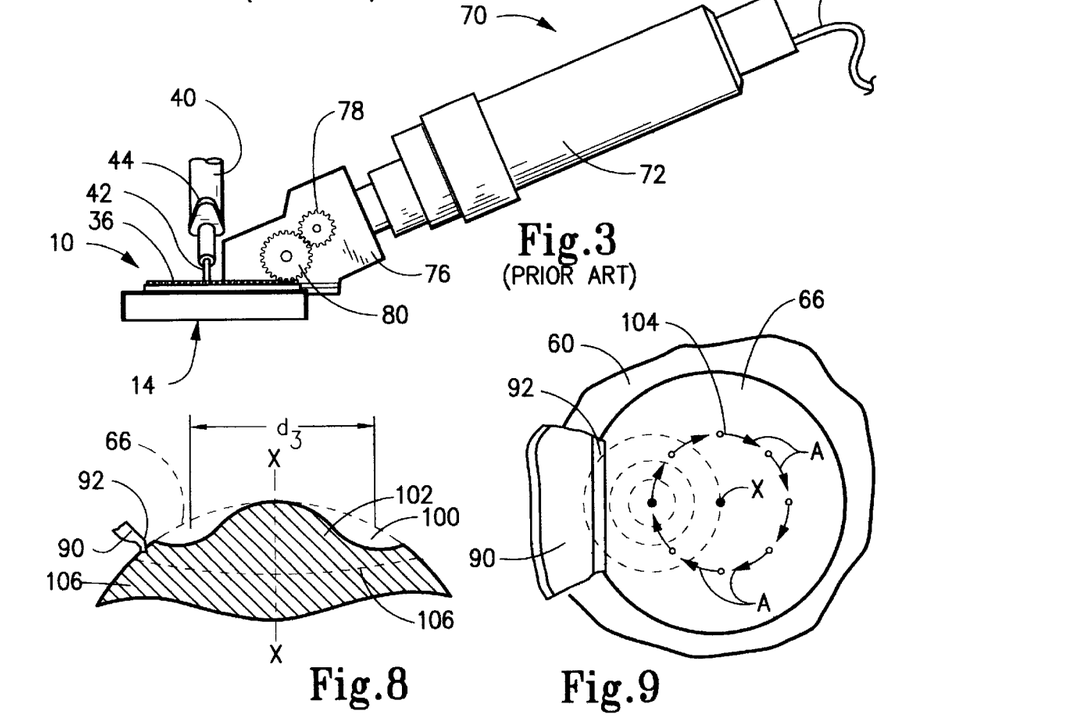
FIG. 3 is a side view in elevation showing a microkeratome according to the prior art mounted in the apparatus of FIGS. 1 and 2 for use in cutting a corneal cap according to the present invention.
FIG. 8 is a side view in cross-section showing the contour cut into the cornea used to correct hyperopia according to the LASIK procedure.
FIG. 9 is a top plan view, similar to FIG. 7, but showing the pattern and control of the laser beam used to cut the contour of FIG. 8.
Figure 4:
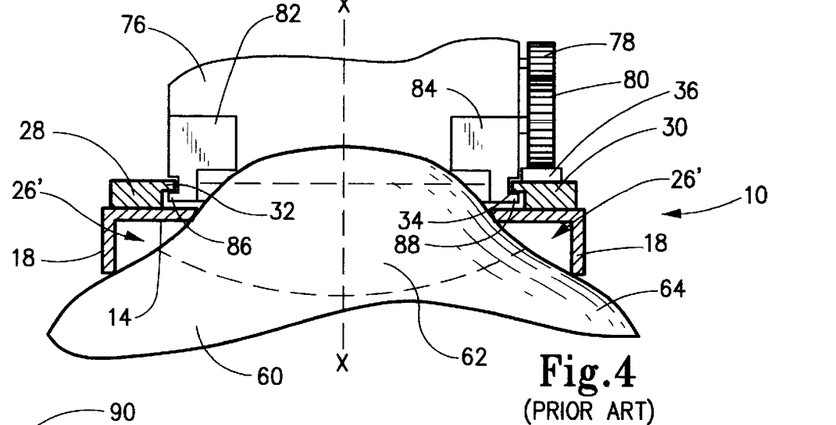
FIG. 4 is a side view, in partial cross-section, of the microkeratome and apparatus of FIGS. 1–3 shown in position to cut a dome-like corneal cap from the cornea of a human eye.

As is shown in FIGS. 1 and 2 mount 10 includes an elongated handle 12 which supports an annular piece 14 at its distal end. Annular piece 14 is formed by an annular plate 16 and a surrounding circular rim 18 which is disposed on plate 16 and is formed integrally therewith. Annular piece 14 has a circular opening 20 formed medially thereof with the circular edge 22 of opening 20 being formed at an obtuse angle with respect to the inner surface 24 located in the cup-shaped interior 26 formed by plate 16 in rim 18. Plate 16 supports a pair of parallel rails 28 and 30 which have opposed lips 32 and 34, respectively which defines a mount of the micro keratome as described below. A rack gear 36 is disposed along rail 30 and provides part of the drive mechanism for the micro keratome. Handle portion 12 includes a shaft 38 on which a sleeve 40 is slideably disposed. Sleeve 40 is spring loaded so that it is biased toward distal end 42 of handle portion 12 with the distal end of sleeve 40 including a wing 44 formed integrally therewith. Shaft 38 includes an axial bore 46 therethrough, and this bore 46 is in fluid communication with a conduit 50 that is connected at a proximal end 48 of handle portion 12 which interconnects mount 10 with a vacuum source (not shown). With reference to FIGS. 3 and 4, it may be seen that annular piece 14 may be placed on a eye 60 so that cornea 62 is positioned through and protrudes out of circular opening 20 in plate 16. Rim 18 contacts surface 64 of eye 60 such that the application of vacuum by way of conduit 50 creates a volume of reduced pressure in the interior region 26' thus holding annular piece 14 on eye 60 by means of the suction created thereby.

A microkeratome 70 is shown in FIGS. 3 and 4 and includes a motor handle 72 connected to a suitable electric source by wires 74 and which is operative to drive a cutting head 76. Suitable gearing is provided to connect motor 72 so that an output gear 78 rotatably drives a drive gear 80 that engages rack gear 36 when microkeratome 70 is secured to mount 10. This is best shown in FIGS. 3 and 4 where it may be seen that cutting head 76 includes a pair of channel pieces 82 and 84 which respectively engage lips 32 and 34 of rails 28 and 30, respectively. To this end, channel pieces 84 include outwardly turned lips 86 and 88, respectively which engage lips 32 and 34. Accordingly, as motor 72 turns gear 78, gear 80 is rotated so that, when engaged, cutting head 76 is advanced across the surface of plate 16 by virtue of rails 28, 30 and channel pieces 82, 84. Cutting head 76 is provided with a blade that is operative to sever a dome-shaped cap from cornea 62 as cutting head 76 is advanced along rails 28 and 30. Typically, the desired diameter of the cap is about eight millimeters.

It should be understood that the construction of mount 10 is shown in simplified form in FIGS. 1–4. However, it is known to include an adjustment plate to select the protrusion of the cornea through opening 20 so that the depth of the cut into the cornea, and thus the thickness of the cap, may be selectively varied. In any event, with reference to FIG. 5, it may be seen that the microkeratome is operative to cut a shell-like cap 90 from the top of cornea 62 while leaving a small flap of tissue 92 that pivotally connects an edge of cap 90 to cornea 62 for maintaining rotational alignment and to reduce the likelihood of cap dislodgement, as described above in the background of the invention. Moreover, the operation of micro keratome 70 provides a curved dome 66 that has a base 67 generally located in a plane "P" that is transverse to the optical axis "X" of the eye.

Figures 5, 6:
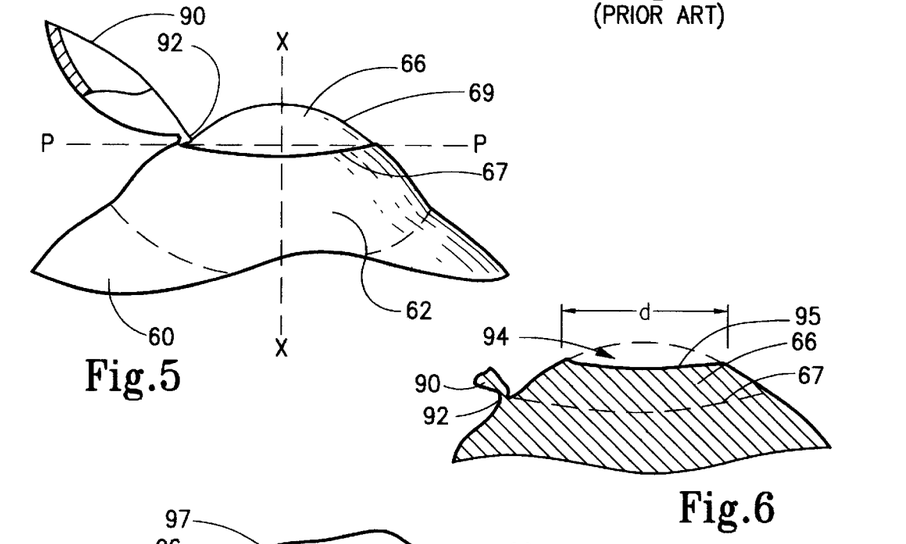
FIG. 5 is a diagrammatic view of a human eye, including the cornea, with the corneal cap being cut and pivoted into an out of the way position according to the ALK and LASIK procedures.
FIG. 6 is a side view in cross-section showing a contour cut into the cornea used to correct myopia according to the LASIK procedure.
Figure 7:
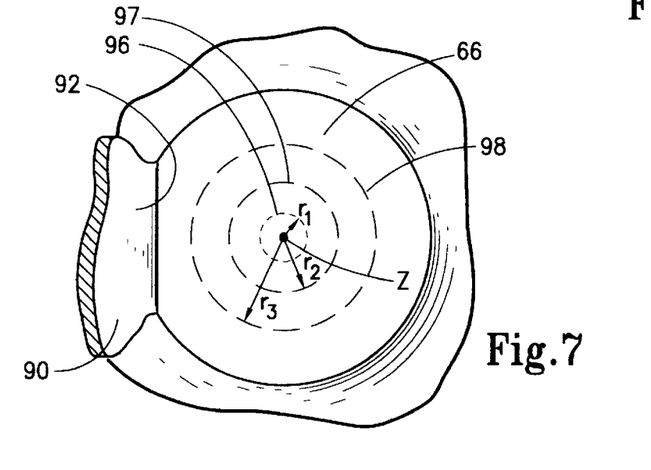
FIG. 7 is a top plan view of a diagrammed cornea showing the laser pattern used to cut the contour of FIG. 6.
Figures 10, 11:
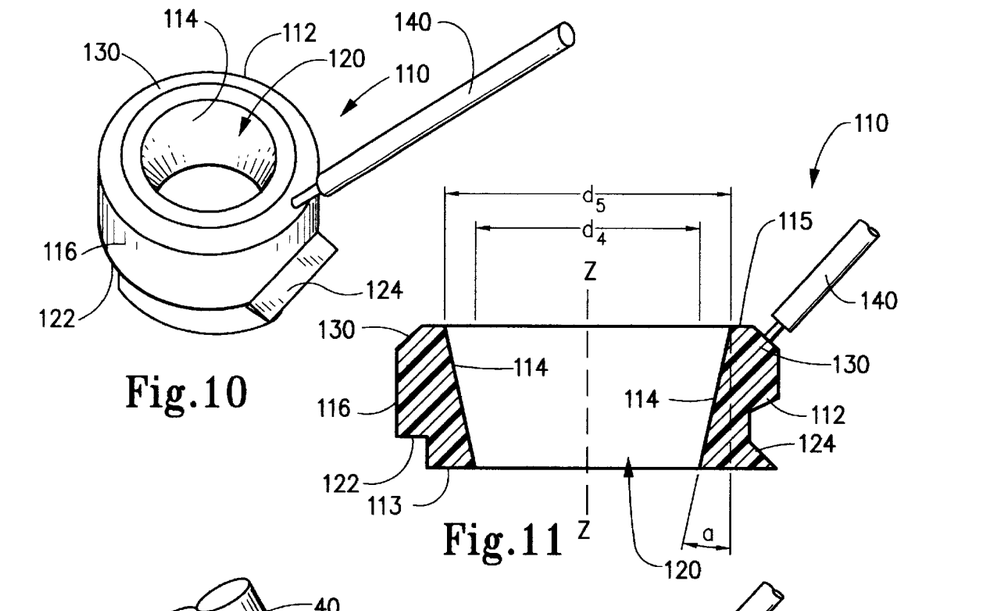
FIG. 10 is a perspective view of the optical guide according to the exemplary embodiment of the present invention.
FIG. 11 is a side view in partial cross-section of the optical guide of FIG. 10.

The LASIK procedure for correcting myopia is best understood, now, with reference to FIG. 6 and 7. Here, it may be seen that the top of dome 64 is removed by cutting a void 94 into surface 69 of dome 64 by means of an excimer-type laser. In order to correct myopia, it is desired that this cavity 94 be shaped so that a greater portion of corneal tissue is removed at a central area. This creates the inverse of a corrective lens of the type that would normally be placed in contact with or approximate to the eye surface. The diameter "d", of this void 94 must be sufficient so that the resulting optical zone of correction is at least 5 millimeters in diameter, although in any event the optical zone should be at least 5 millimeters in diameter.

With reference to FIG. 7, it may be seen that the procedure for cutting this cavity 94 is accomplished by directing a beam of laser light at a reduced radius "$r_1$" that is at relatively high intensity. After a desired period, depending upon the depth of the cavity to be formed, the beam size is increased to a larger radius, such as "$r_2$" and thereafter to an even still larger radius, such as radius "$r_3$" after which the laser beam may be discontinued. This creates circular cut regions or concavities 96, 97, 98, respectively, although it should be appreciated that the expansion of the size of the laser beam may be either continuous or by very small increments.

Thus, a relative uniform concavity having its greatest depth at a central point is made. This is due to the fact that the central portion of the cornea is constantly exposed to the incident laser beam with the greatest intensity being at the center while the lowest intensity being at the peripheral edge of cavity 94. This results both to the fact that the beam is focused more intensely at the beginning, but also to the property of laser light in having an intensity distribution that is in an Gaussian distribution with peak intensity being at the center of the laser beam. After forming cavity 94, cap 90 is replaced onto surface 66 and is healed into contact with the inner contour 95 of cavity 94. By removed corneal tissue at void 94, the shape of cap 90 when replaced is flattened. Since this results in a larger radius of curvature, i.e., a less steep corneal surface, the cornea has a longer focal length. Thus, light passing through the eye optics becomes focused on the retina.

At this juncture, it is appropriate to consider that the desired maximum diameter of the cavity 94 is approximately 6 millimeters. This corresponds to an optical zone that is sufficient to avoid edge effects when light rays pass through the healed cornea. Thus, it should be understood that the excimer-type laser typically starts at a diameter of about 1 millimeter and expands as it pulses to a maximum diameter of 6 millimeters. Further, the laser can be moved slightly during the formation of cavity 94 so that it ends up to be oval in configuration thereby correcting for astigmatism.

The correction of hyperopia, however, presents a much more difficult problem. With reference to FIGS. 8 and 9, it may be seen that the desired cavity for hyperopia is concave in shape. Thus, cavity 100 is annular in shape having a maximum depth along a circle that is spaced from central area 102 of cornea 62. This is accomplished by focusing the laser beam along an axis that is parallel to but offset from central axis "X" of the eye and tracking the beam around axis "X" at the selected radial distance, shown by arrows "A" in FIG. 9. The beam width is then expanded from a diameter of approximately 1 millimeter to 5 millimeters while it revolves around the axis "X".

It may now be appreciated that a difficulty resides in the formation of cavity 100. In order to provide an optical zone that is at least 5 millimeters, it is necessary to center the laser beam approximately 2.5 millimeters radially from optical axis "X" and expand it to 5 millimeters diameter. Accordingly, the zone size which would be cut would become approximately 10 millimeters in diameter, corresponding to the 5 millimeters beam width at 180° spacing around axis "X". Using a laser beam that is expanded to an amount less than 5 millimeters cuts an effective optical zone that is too small so that the patient would notice edge effects in his/her visual correction. However, by expanding the laser to 5 millimeters, a portion of the surgical light can extend outside of the 8 millimeter width of cap 90 so that a resulting removal of tissue would be along the line 106 shown in phantom in FIG. 8. This is undesirable since the peripheral margin of cavity 100 would not be at the desired steepness while at the same time, such a cut would damage the flap 92 and dome structure 90 during formation of cavity 100. The present invention provides a guide and method for eliminating this problem.

The invention, therefore, is best shown in FIGS. 10–13. Here, optical guide 110 includes a body portion 112 that is annular in configuration so as to have an inner sidewall 114 and an outer sidewall 116. An axial passageway 120 extends through body portion 112 width this passageway being defined by a surrounding sidewall 114. Preferably, axial passageway 120 is frustoconical in shape with sidewall 114 therefore being divergent from bottom surface 113 to top surface 115. Passageway 120 thereby has a minimum optical opening diameter "$d_4$" which is approximately 8 millimeters and which has a maximum optical opening diameter "$d_5$" which is approximately 10 millimeters. Thus, it may be seen in reference to FIGS. 11 and 12 each side of that passageway 120 diverges at an acute angle "a" that is approximately 15° in a direction away from the eye along central axis "C". Accordingly, sidewall 114 diverges at a total angle of divergence of approximately "$2a$", that is, about 30°.

Thus, the cross-section of passageway 120 has a periphery of a selected configuration through which the laser light may pass, and it is to be understood that body portion 12 is constructed of a material that is effective in dispersing the laser light which is incident thereto. That is, this material is suitable either to absorb, refract or reflect the laser light in such a manner that its energy is dissipated to a level that will not affect eye tissues.

Figure 12:
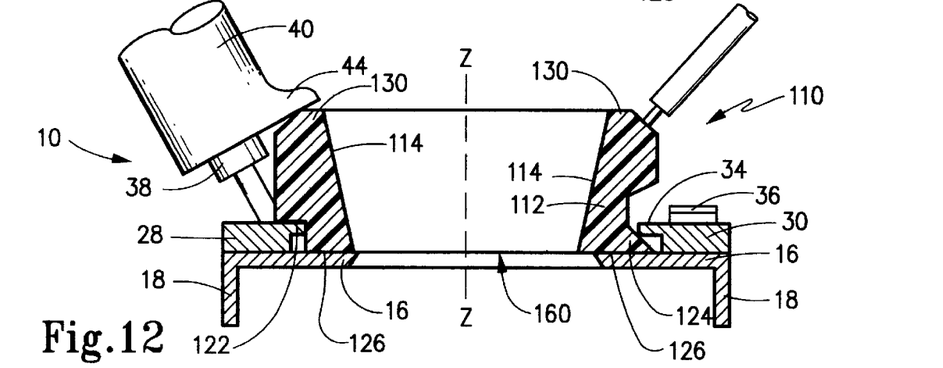
FIG. 12 is a side view in partial cross-section showing the optical guide of FIGS. 10 and 11 mounted in the positioning apparatus of FIGS. 1 and 2.

A lower portion of optical guide 110 is provided with an engagement structure that assists in securing optical guide 110 to mount 10. Here, it may be seen that shoulder 122 is provided to be positioned proximate to rail 28 while a foot 124 is oppositely disposed relative to shoulder 122 and is provided to extend under lip 34 when lower surface 126 of body portion 112 is placed in contact with plate 16. Body portion 112 is further held in position by means of a retaining element in the form of a resiliently biased sleeve 40 with a wing 44 contacting a rim 130 of body portion 112. Moreover, in order to help manipulate optical guide 110, a handle 140 is secured to rim 130 on a side thereof corresponding to foot 124. Handle 140 is operative to facilitate manipulation and positioning of body portion 112.

Figure 13:
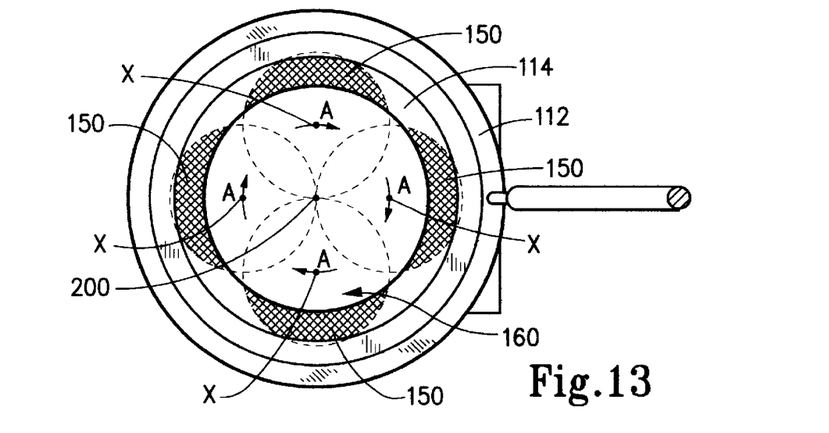
FIG. 13 is a top plan view of the optical guide of FIGS. 10–12 also diagramming its affect on the laser control pattern of FIG. 9 in order to cut the corrective contour of FIG. 8.

With reference, now, to FIG. 13 it may be seen that the optical guide acts to shield the laser light outside of the desired zone of 8 millimeters. As laser light is directed for cutting cavity 100, crescent-shaped portions 150 of the laser light are blocked from being incident onto surface 66 of the cornea. Rather, these crescent-shaped portions 150 will be incident onto body portion 112, such as along sidewall 114 and will be dissipated so as to have no cutting affect on the area of the cornea outside of the optical opening 160 formed by the minimum geometric diameter "$d_4$". The frustoconical or funnel shape of passageway 120 moreover eliminates the need to have the passageway oriented perfectly along the optical axis or to have it oriented perfectly with respect to the incident laser light. As noted, it is important that the material selected for central body portion 112 be suitable to dissipate the energy of the laser light to a level that will not affect eye tissues. Accordingly, this material must be selected with the wavelength of the laser light taken into consideration. In the LASIK procedure, the excimer-type laser typically operates at a wavelength of 193 microns. A material which has been found preferable for the construction of body portion 112, then, is methymethacrylate. Other plastics, such as polytetrafluoroethylene polymers, may well be employed to construct body portion 112, and even glass may be used, as would be apparent to the ordinarily skilled person.

From the foregoing, it should be appreciated that the present invention also includes a method of corrective surgery for hyperopia. Broadly, this method comprises a first step of preparing an eye to have an exposed section of corneal tissue. This is preferably accomplished by cutting a shell-like cap from the surface of the cornea, such as cap 90, as is illustrated in FIG. 5. This leaves a curved dome 66 as an exposed section of corneal tissue. The base 67 of this dome structure is preferably about 8.0 millimeter in diameter. After preparation of the eye to have an exposed section of corneal tissue, an optical guide, preferably such as that described above, is disposed proximate to the exposed section of corneal tissue. As noted above, this optical guide includes a body portion having an axial passageway therethrough which permits unobstructed passage of axial laser light to an operative region surrounded by a sidewall of the optical guide. The operative region thus has a surrounding periphery of a selected configuration and a center point 200 (FIG. 13) that is located on axis "C".

Next, a beam of laser light at a selected energy sufficient to remove corneal tissue cells is directed along an optical path, such as "X" (FIG. 13) that is parallel to a central axis "Z". With this step, the laser beam is incident to the exposed section of corneal tissue with the beam of laser light, of course, having a central area of maximum intensity. The beam of laser light is sized at some point during the laser eye surgery to have a diameter that is greater than a radial dimension of the operative region. The beam is positioned so that the central area thereof is offset from the center point 200 whereby an active portion of the light will pass through the axial passageway and wherein an inactive portion of the light will be incident to the body portion of the optical guide. The guide, as noted above, is constructed of a material that is effective in disbursing the energy of laser light to a level that will not remove corneal tissue cells. Finally, the beam of laser light is moved along a pathway that surrounds the central point. Thus, the laser light is used to form a recess by removal of corneal tissue cells with the recess having a greatest depth along the pathway.

Preferably, during the surgery, the diameter of the beam is varied as it is moved along the pathway. This is similar to the variance in radii $R_1$–$R_3$, such as shown in FIG. 7. However, in FIG. 7, the beam is centered and remains centered, along central axis "Z" as, with reference to FIG. 13, it may be seen that in the method of correcting hyperopia, the beam is offset from the central axis. Nonetheless, the beam is moved along the pathway while varying the diameter of the beam. Preferably, the beam is expanded as it is moved along the pathway, although it would be possible to start larger and constrict beam as it is moved therealong. In any event, it is preferred that the central area of the laser beam is disposed approximately 2.5 to 3.5 millimeters from the center point and that diameter of the beam is varied between 1.0 millimeter and 5.0 millimeter. The pathway in which the beam is moved may be circular, but, where astigmatism is desired to be simultaneous corrected, the pathway may be designed to be ovoid to remove the oblong configuration.

If desired, variably contoured surfaces may be formed on the globe portion of the eye by varying the energy of the laser over the pathway. this is done, generally, by two methods. First, the speed at which the laser beam tracks around the pathway can be varied along different segments. Alternatively, the pulse rate and thus the duty cycle of the laser can be made different along different segments of the pathway.

Accordingly, the present invention has been described with some degree of particularity directed to the exemplary embodiment of the present invention. It should be appreciated, though, that the present invention is defined by the following claims construed in light of the prior art so that modifications or changes may be made to the exemplary embodiment of the present invention without departing from the inventive concepts contained herein.

I claim:

1. An optical guide adapted for use in laser surgery of an eye and operative to disperse laser light of a selected energy which is incident outside of a selected region, said optical guide comprising a body having a passageway therethrough and a sidewall surrounding said passageway, said passageway having a selected geometrical cross-section that defines a minimum optical opening having a periphery of a selected configuration through which the laser light may pass, said body constructed of a material that is effective in dispersing the laser light which is incident thereto such that the energy thereof is dissipated to a level that will not affect eye tissues.

2. An optical guide according to claim 1 wherein said body is annular in shape with said passageway defined by an inner sidewall of said body.

3. An optical guide according to claim 2 wherein said passageway is frustoconical in shape such that said sidewall is angularly divergent.

4. An optical guide according to claim 3 wherein said sidewall has an angle of divergence of about thirty degrees.

5. An optical guide according to claim 3 wherein said passageway is frustoconical in shape such that said sidewall is angularly divergent.

6. An optical guide according to claim 1 wherein the passageway extends axially through said body.

7. An optical guide according to claim 1 wherein said body portion is fabricated of a plastic material.

8. An optical system adapted for use in corrective eye surgery wherein focusing optics directs a beam of laser light from a laser light source of a selected energy along an optical path that is incident onto tissues of an eye, said energy being such that cellular eye tissue is removed by the laser light directly incident thereto, and wherein a control system is provided to control the size of the beam of laser light and a tracking path therefor, said optical system comprising:

(a) a mount operative to be placed in contact with the eye over a region targeted for laser surgery; and (b) an optical guide adapted to be secured to said mount, said optical guide including a body portion having an axial passageway extending therethrough between a top and a bottom thereof and an inner sidewall surrounding said axial passageway, said axial passageway having a selected geometrical cross-section that defines a minimum optical opening having a periphery of a selected configuration through which the laser may pass in an axial direction, said body constructed of a material that is effective in dispersing the laser light which is incident thereto such that the energy thereof is dissipated to a level that will not affect eye tissues.

9. An optical guide according to claim 8 wherein said body is annular in shape with said passageway defined by an inner sidewall of said body.

10. An optical guide according to claim 8 wherein said mount is a suction ring.

11. A method of performing laser eye surgery for correction of hyperopia comprising the steps of:

(a) preparing an eye to have an exposed section of corneal tissue;

(b) disposing an optical guide proximate to said section of corneal tissue, said optical guide including a body portion having an axial passageway therethrough which permits unobstructed passage of axial laser light through an operative region surrounded by a sidewall of said optical guide, said operative region having a surrounding periphery of a selected configuration and a center point with said axial passageway having a central axis passing through the center point;

(c) directing a beam of laser light at a selected energy sufficient to remove corneal tissue cells along an optical path that is parallel to the central axis such that said laser beam is incident to said exposed section with said beam of laser light having a central area of maximum intensity, said beam of laser light being sized to have a diameter that is greater than a radial dimension of the operative region and positioned such that the central area thereof is offset from the center point whereby an active portion of light will pass through said axial passageway and wherein an inactive portion of said laser light will be incident to said body portion, said sidewall constructed of a material that is effective in dispersing the energy of said laser cells; and (d) moving the beam of laser light such that the central area thereof follows a pathway that surrounds the central point whereby a recess is formed by removal of corneal tissue cells, said recess having a greatest depth along a medial area of the pathway.

12. A method according to claim 11 wherein the diameter of said beam is varied as said beam is moved along the pathway.

13. A method according to claim 12 wherein the diameter is expanded as said beam is moved along the pathway.

14. A method according to claim 12 wherein said central area is disposed 2.5–3.5 millimeters from the center point.

15. A method according to claim 14 wherein the diameter of said beam is varied between 1.0 millimeters and 5.0 millimeters.

16. A method according to claim 11 wherein said pathway is a geometrical shape selected from a group consisting of: circular pathways and ovoid pathways.

17. An optical guide adapted for use in laser surgery of an eye and operative to disperse laser light of a selected energy which is incident outside of a selected region, said optical guide comprising:

(a) a body having a passageway therethrough and a sidewall surrounding said passageway, said passageway having a selected geometrical cross-section that defines a minimum optical opening having a periphery of a selected configuration through which the laser light may pass, said body constructed of a material that is effective in dispersing the laser light which is incident thereto such that the energy thereof is dissipated to a level that will not affect eye tissues; and (b) a handle member secured to said body and operative to facilitate manipulation thereof.

18. An optical guide adapted for use in laser surgery of an eye and operative to disperse laser light of a selected energy which is incident outside of a selected region, said optical guide comprising a body having a passageway therethrough and a sidewall surrounding said passageway, said passageway having a selected geometrical cross-section that defines a minimum optical opening having a periphery of a selected configuration through which the laser light may pass, said body constructed of a material that is effective in dispersing the laser light which is incident thereto such that the energy thereof is dissipated to a level that will not affect eye tissues, said material being selected from a group consisting of plastic and glass.

19. An optical system adapted for use in corrective eye surgery wherein focusing optics directs a beam of laser light from a laser light source of a selected energy along an optical path that is incident onto tissues of an eye, said energy being such that cellular eye tissue is removed by the laser light directly incident thereto, and wherein a control system is provided to control the size of the beam of laser light and a tracking path therefor, said optical system comprising:

(a) a mount operative to be placed in contact with the eye over a region targeted for laser surgery, said mount including a pair of parallel rail elements in spaced-apart facing relationship; and (b) an optical guide adapted to be secured to said mount and including an engagement structure sized and configured to engage said rails thereby to assist in securing said optical guide to said mount, said mount further including a body portion having an axial passageway extending therethrough between a top and bottom thereof and an inner sidewall surrounding said axial passageway, said axial passageway having a selected geometrical cross-section that defines a minimum optical opening having a periphery of a selected configuration through which the laser may pass, said body constructed of a material that is effective in dispersing the laser light which is incident thereto such that the energy thereof is dissipated to a level that will not affect eye tissues.

20. An optical guide according to claim 19 wherein said engagement structure includes a foot portion operative to engage one of said rails.

21. An optical guide according to claim 20 wherein said engagement structure includes a shoulder portion disposed oppositely of said foot portion and operative to engage another of said rails, said mount including a retaining element operative to bear against said body portion to retain said body portion to retain said foot and shoulder portions in engagement with said rails.

22. An optical guide according to claim 21 wherein said retaining element is resiliently biased against said body portion when said optical guide is secured to said mount.

* * * * *